US008224048B2

(12) United States Patent
Hou et al.

(10) Patent No.: US 8,224,048 B2
(45) Date of Patent: Jul. 17, 2012

(54) COMPUTER IMPLEMENTED METHOD FOR CORRECTION OF MAGNETIC RESONANCE IMAGES

(75) Inventors: Zujun Hou, Singapore (SG); Su Huang, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 959 days.

(21) Appl. No.: 12/093,933

(22) PCT Filed: Nov. 21, 2006

(86) PCT No.: PCT/SG2006/000356
§ 371 (c)(1),
(2), (4) Date: Jul. 31, 2008

(87) PCT Pub. No.: WO2007/058631
PCT Pub. Date: May 24, 2007

(65) Prior Publication Data
US 2009/0046915 A1    Feb. 19, 2009

Related U.S. Application Data
(60) Provisional application No. 60/738,070, filed on Nov. 21, 2005.

(51) Int. Cl.
*G06K 9/00* (2006.01)
(52) U.S. Cl. ...................................... 382/128
(58) Field of Classification Search ........... 382/100–150
See application file for complete search history.

(56) References Cited

U.S. PATENT DOCUMENTS

| | | | |
|---|---|---|---|
| 5,903,664 A * | 5/1999 | Hartley et al. | 382/154 |
| 5,943,433 A | 8/1999 | Avinash | |
| 6,208,138 B1 | 3/2001 | Lai et al. | |
| 6,980,682 B1 * | 12/2005 | Avinash et al. | 382/131 |
| 7,053,612 B2 | 5/2006 | St. Pierre et al. | |
| 7,110,588 B2 * | 9/2006 | Dewaele et al. | 382/132 |
| 7,382,908 B2 * | 6/2008 | Dewaele et al. | 382/132 |
| 7,460,709 B2 * | 12/2008 | Grady | 382/180 |
| 7,545,979 B2 * | 6/2009 | Fidrich et al. | 382/173 |
| 7,798,643 B2 * | 9/2010 | Waldorf et al. | 351/209 |
| 7,835,577 B2 * | 11/2010 | Grady | 382/173 |
| 7,990,379 B2 * | 8/2011 | Aharon et al. | 345/424 |

FOREIGN PATENT DOCUMENTS
WO    WO-2004/059335 A1    7/2004

OTHER PUBLICATIONS

Brinkman, B. H. et al. (Apr. 1998). "Optimized Homomorphic Unsharp Masking for MR Grayscale Inhomogeneity Correction," *IEEE Transactions on Medical Imaging* 17(2):161-171.
International Search Report mailed Jan. 23, 2007, for PCT Application No. PCT/SG2006/00356 filed Nov. 21, 2006, 3 pages.

* cited by examiner

*Primary Examiner* — Dixomara Vargas
(74) *Attorney, Agent, or Firm* — Morrison & Foerster LLP (57) ABSTRACT

A method of correcting magnetic resonance images is provided. Seed points having a same expected true intensity are selected from the image points in an image. An intensity correction function $I_f(X)$ is determined by fitting measured intensities $I_m(X_s)$ of the seed points to $I_m(X_s)=I_f(X_s)$, where x denotes the coordinate of the image points. $I_f(X)$ is a polynomial function and the values of its coefficients are determined by the fitting. Corrected intensities $I_c(X_c)$ for corrected image points are calculated according to $I_c(X_c)=I_m(X_c)/I_f(X_c)$. A corrected image includes the corrected image points.

26 Claims, 9 Drawing Sheets

COMPUTER IMPLEMENTED METHOD FOR CORRECTION OF MAGNETIC RESONANCE IMAGES

CROSS REFERENCE TO RELATED APPLICATIONS

This application is a U.S. National Phase of PCT/SG2006/000356, filed Nov. 21, 2006, which claims the benefit of U.S. Provisional Application No. 60/738,070, filed Nov. 21, 2005, the contents of which are hereby incorporated by reference in the present disclosure in their entirety.

FIELD OF THE INVENTION

The present invention relates to methods and devices for image correction, and more particularly, for inhomogeneity correction in magnetic resonance (MR) images.

BACKGROUND OF THE INVENTION

The measured intensities in an MR image, such as a brain image, are dependent on both the background noise and the local magnetic field. The degree of variation of the local magnetic fields at different locations in space is referred to as magnetic field inhomogeneity. Thus, the measured intensities of the image points can be different from the "true" intensities, which are the intensities one would have been obtained if there were no background noise and the magnetic field is homogenous, i.e. uniform over the imaged region. Field inhomogeneity can cause reduced image contrast and increased tissue variance. Thus, it is desirable to correct for the field inhomogeneity.

There are many conventional techniques for inhomogeneity correction. Typically, the measured image is segmented, either manually or automatically. The segmented image is then processed to estimate the inhomogeneity, represented as a map known as the inhomogeneity map.

For example, in one conventional technique, it is assumed that noise can arise randomly independent of the true image intensity but the field inhomogeneity contribution is dependent on the true image intensity. Thus, a measured image intensity ($I_m$) can be expressed as:

$$I_m(x) = f_b(x) I_t(x) + I_n(x), \quad (1)$$

where x is the coordinate of the location of the image pixel or voxel, $I_t$ is the true image intensity, $I_n$ is the noise intensity, and $f_b$ is an unknown bias field, which may vary at different locations. Inhomogeneity correction thus involves estimating the bias field $f_b$. In this technique, the bias field is assumed to be multiplicative and smoothly, slowly varying. The multiplicative bias field and the distribution of the true intensities are simultaneously estimated using an iterative approach, by maximizing the frequency content of the true intensity distribution.

Some conventional inhomogeneity correction techniques are discussed in B. Likar et al., "Retrospective correction of MR intensity inhomogeneity by information minimization", *IEEE Transactions on Medical Imaging*, 2001, vol. 20, pp. 1398-1410; M. N. Ahmed et al., "A modified FCM algorithm for bias field estimation and segmentation of MRI data", *IEEE Transactions on Medical Imaging*, 2002, vol. 21, pp. 193-199; B. Dawant et al. "Correction of intensity variations in MR images for computer-aided tissue classification", *IEEE Transactions on Medical Imaging*, 1993, vol. 12, pp. 770-781; W. M. Wells et al/, "Adaptive segmentation of MRI data", *IEEE Transactions on Medical Imaging*, 1996, vol. 15, pp. 429-442; R. Guillemaud and M. Brady, "Estimating the bias field of MR images", *IEEE Transactions on Medical Imaging*, 1997, vol. 16, pp. 238-251; J. C. Rajapakse and F. Kruggel, "Segmentation of MR images with intensity inhomogeneities", *Image and Vision Computing*, 1998, vol. 16, pp. 165-180; D. L. Pham and J. L. Prince, "Adaptive fuzzy segmentation of MR images", *IEEE Transactions on Medical Imaging*, 1999, vol. 18, pp. 737-752; Sled et al., "A nonparametric method for automatic correction of intensity nonuniformity in MRI data", *IEEE Transactions on Medical Imaging*, 1998, vol. 17, pp. 87-97; J. B. Arnold, J. S. Liow et al., "Qualitative and quantitative evaluation of six algorithms for correcting intensity nonuniformity effects", *NeuroImage*, 2001, vol. 13, pp. 931-943.

However, conventional techniques have some drawbacks. One problem is that when the noise is relatively large, inhomogeneity correction obtained from these techniques is often inaccurate. Another problem is that it can take a relatively long time to complete an inhomogeneity correction using conventional techniques.

SUMMARY OF THE INVENTION

In accordance with an aspect of the present invention, there is provided a method of correcting a magnetic resonance (MR) image comprising a plurality of image points. Each image point has a coordinate x and a measured intensity $I_m(x)$ dependent on x. The method comprises selecting seed points having a same expected true intensity from the image points, each seed point having a coordinate $x_s$; determining an intensity correction function $I_f(x)$ by fitting measured intensities of the seed points to $I_m(x_s) = I_f(x_s)$, $I_f(x)$ being a polynomial function having coefficients, wherein values of the coefficients are determined by the fitting; and obtaining a corrected image comprising corrected image points that have corrected intensities $I_c(x_c)$, $I_c(x_c)$ being calculated according to $I_c(x_c) = I_m(x_c)/I_f(x_c)$.

Values of the coefficients of the intensity correction function may be stored. The stored values may include values of $I_f(x)$. The corrected image may be stored. The corrected image may be displayed. The MR image may be corrected by substituting $I_m(x_c)$ with $I_c(x_c)$ for the corrected image points. $I_f(x)$ may have a degree of 2. $I_f(x)$ may have a form selected from $I_{f1}(x) = I_0 + f(x)$ and $I_{f2}(x) = [1+f(x)]I_0$, where f(x) is a polynomial function, and $I_0$ is one of the coefficients determined by the fitting. The coordinate x may comprise Cartesian x, y and z coordinates, and f(x) may have the form of:

$$f(x) = f(x,y,z) = p_{1,0,0}x + p_{0,1,0}y + p_{0,0,1}z + p_{2,0,0}x^2 + p_{0,2,0}y^2 + p_{0,0,1}z^2 + p_{1,1,0}xy + p_{1,0,1}xz + p_{0,1,1}yz.$$

The coordinate x may comprises Cartesian x and y coordinates, and f(x) may have the form of: $f(x) = f(x,y) = p_{1,0}x + p_{0,1}y + p_{2,0}x^2 + p_{0,2}y^2 + p_{1,1}xy$. The plurality of image points may represent a plurality of classes of imaged matter, and the selection of the seed points may comprise selecting seed blocks from a continuous region in the MR image, the continuous region dominated by image points representing one class of imaged matter, each seed block having a plurality of image points; and selecting an image point from each seed block as one of the seed points. Exactly one of the seed points may be selected from each one of the seed blocks. Each seed block may have a central image point, and the central image point may be selected as one of the seed points. The seed blocks may be isolated from each other. The seed blocks may be distributed throughout the continuous region. The seed blocks may have a same shape and a same size. The MR image may be three-dimensional and the shape of blocks may be a cube. The cube may consist of 125 image points. The MR image may be two-dimensional and the shape of the blocks may be a square. The square may consist of 25 image points. The continuous region may be formed of candidate blocks and selection of the seed blocks may comprise identifying the candidate blocks from the MR image, the identifying comprising determining blocks that each consists of image points having measured intensities of a range statistic less than a range threshold; and selecting the seed blocks from the candidate blocks. The range threshold may be selected so that image points in each candidate block are expected to represent one class of imaged matter. The range statistic may be a normalized range statistic. The normalized range statistic may be less than 0.5. Each candidate block may neighbor at least another candidate block. The image points in each candidate block have an average intensity, and an absolute difference between the average intensities of each pair of neighboring candidate blocks may be less than a threshold. The plurality of image points of the MR image may be within a region of interest in the MR image.

In accordance with another aspect of the invention, there is provided a computer-readable medium storing computer executable instructions that, when loaded at a computer, adapting the computer to perform the method of described above.

In accordance with another aspect of the invention, there is provided a computer comprising a processor and a memory in communication with the processor, the memory storing computer executable instructions that, when executed by the processor, adapt the computer to perform the method described above.

Other aspects and features of the present invention will become apparent to those of ordinary skill in the art upon review of the following description of specific embodiments of the invention in conjunction with the accompanying figures and tables.

BRIEF DESCRIPTION OF THE DRAWINGS

In the figures, which illustrate, by way of example only, embodiments of the present invention.

DETAILED DESCRIPTION

In overview, it is now discovered that it is possible to quickly estimate field inhomogeneity from a magnetic resonance (MR) image in the presence of even large background noise, when the background noise is randomly distributed in space and the field inhomogeneity is slowly and smoothly varying over space. This result may be achieved by correcting the MR image using an intensity correction function $I_f(x)$. Intensity correction function $I_f(x)$ is a polynomial function of the coordinate x and has coefficients whose values are determined by fitting as described below. A generalized corrected intensity $I_c(x)$ of each corrected image point in a given region of the image is calculated as:

$$I_c(x)=I_m(x)/I_f(x), \qquad (2)$$

where $I_m(x)$ is the measured intensity at the image point of coordinate x, and $I_c(x)$ may be either an absolute corrected intensity or a normalized corrected intensity, depending on the form of $I_f(x)$, as will be further described below. For clarity, it should be understood that the bold letters are not used herein to indicate vectors. In some embodiments, not all image points in the MR image need to be corrected and only selected image points are corrected. In such cases, the coordinate of the corrected image points may be denoted as $x_c$, and Equation (2) may be alternatively expressed as $I_c(x_c)=I_m(x_c)/I_f(x_c)$. It should be understood that $x_c$ and x may or may not represent the same set of image points.

The intensity correction function $I_f(x)$ may have either of the following forms in Equations (3) or (4), which are equivalent as can be understood by persons skilled in the art:

$$I_{f1}(x)=I_0+f_1(x), \qquad (3)$$

or $$I_{f2}(x)=[1+f_2(x)]I_0, \qquad (4)$$

where $I_0$ is a coordinate-invariant constant, and each of $f_1(x)$ and $f_2(x)$ is a polynomial function that has no zero-order term.

A polynomial function that has no zero-order term is denoted herein as f(x). The variables in f(x) are the coordinates. Thus, the function f(x) is a sum of two or more terms, where each term is the product of a parameter (collectively referred to as parameter "p" herein) and one or more coordinates, depending on the dimension of the coordinate x. For example, if x includes the three Cartesian coordinates, i.e., x=(x, y, z), each term of function f(x) will have the general form:

$$\text{Term}_{i,j,k}=p_{i,j,k}x^iy^jz^k, \qquad (5)$$

where each of i, j, and k is a non-negative integer. The sum of i, j, and k, which is the order of the term, is always greater than zero, as f(x) has no zero-order term.

The order or degree of the polynomial function f(x) may be 1 or higher. As can be understood, the degree of f(x) is also the degree of the intensity correction function $I_f$. In different embodiments, the degree of f(x) or $I_f$ may vary, such as being 1, 2, 3, or higher. For example, in one embodiment, the polynomial function $I_f$ may have a degree of two.

The form of f(x) may vary depending on the type of the MR image to be corrected. For instance, following the above example in Equation (5), the function f(x) having a degree of 2 may have the form:

$$f(x,y,z) = p_{1,0,0}x + p_{0,1,0}y + p_{0,0,1}z + p_{2,0,0}x^2 + p_{0,2,0}y^2 + p_{0,0,1}z^2 + p_{1,1,0}xy + p_{1,0,1}xz + p_{0,1,1}yz. \quad (6)$$

Optionally and depending on the application, f(x) may be simplified and certain parameters may be chosen, i.e., forced, to have a zero value. Alternatively, the fitting to f(x) may be subject to one or more constraints, which may be selected based on some known factors. An exemplary constrain may be that the values of certain parameters are within a particular range. Such constraints may be used to produce more physically meaningful result, or to improve fitting speed such as by reducing the number of iteration cycles.

If the MR image is two-dimensional (2D), x may include two Cartesian coordinates, x=(x, y), and Equation (6) may be reduced to:

$$f(x,y) = p_{1,0}x + p_{0,1}y + p_{2,0}x^2 + p_{0,2}y^2 + p_{1,1}xy. \quad (7)$$

The parameters $I_0$ and p are the coefficients of the polynomial function $I_f$. As can be appreciated, $I_0$ may be interpreted as the base intensity due to the base field. While $f_1(x)$ and $f_2(x)$ each may have the form of f(x), they may have different physical significance. It may be interpreted that $f_1(x)$ represents the intensity contribution due to field inhomogeneity, and $f_2(x)$ represents the coordinate-dependent field variation. While $I_{f1}(x)$ and $I_{f2}(x)$ differ in form, they are equivalent for the purpose of extracting the field inhomogeneity function, where the fitted parameters p in the two cases only differ by a constant ratio $I_0$ for the same data set. That is, $I_{f1}(x) = [1+f_1(x)/I_0]I_0$, and $f_2(x) = f_1(x)/I_0$.

In any case, the coefficients of $I_f(x)$, including the values of p and $I_0$, are determined by fitting measured intensity values of selected image points, referred to as seed points herein, to the following equation, $$I_m(x_s) = I_f(x_s), \quad (8)$$

where $x_s$ represents the coordinate of the seed points.

The seed points are selected so that they all have a same expected "true" intensity ($I_t$). As discussed above, the "true" intensity of an image point is the intensity one would have measured if there was no background noise and the magnetic field in the imaged region was homogenous, i.e., uniform over the imaged region. In one embodiment, the seed points may be isolated from each other and are distributed throughout a continuous region that is expected to represent a same class of imaged matter. The selection of seed points will be further described below. As will become clear below, the seed points are selected based on the expectation that they have the same true intensity, but it is possible that a particular seed point does not actually have the same true intensity as other seed points. Such a seed point may be referred to as a false seed point. As long as the number of such false seed points is small relative to the total number of seed points, good results can still be obtained. As will be described below, some measures may be taken to reduce the number of false seed points.

As can be understood, the values of $I_c(x)$ obtained from Equations (2) and (3) are normalized corrected intensities. In contrast, the values of $I_c(x)$ obtained from Equations (2) and (4) are absolute corrected intensities and may be used directly as the inhomogeneity corrected intensities for the image points.

While in the above intensity correction method the background noise is ignored, the seed points can be selected such that the estimated inhomogeneity function is sufficiently accurate to produce a satisfactory intensity inhomogeneity correction of the MR image. Since it is not necessary to estimate or calculate the background noise in this method, the inhomogeneity function may be obtained quickly with sufficient accuracy even when large noise is present.

Exemplary embodiments of the present invention include methods or processes of magnetic resonance image correction. These methods can be performed, at least in part, by a computing device such as a computer 100 for image processing shown in FIG. 1, exemplary of embodiments of the present invention.

Figure 1:
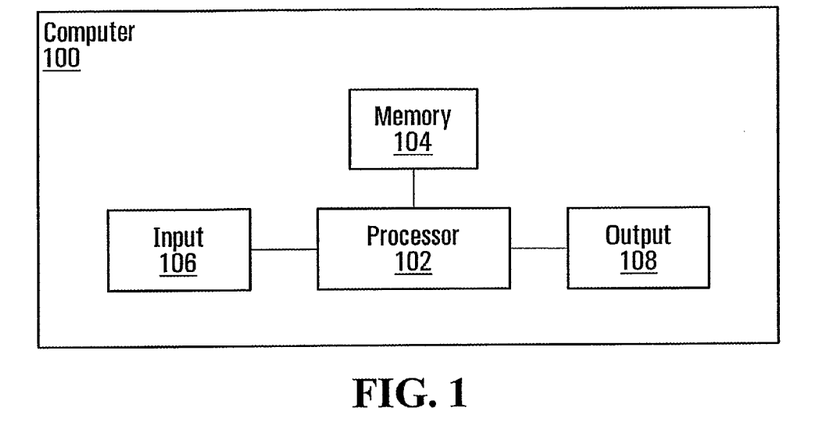
FIG. 1 is a block diagram of a computer, exemplary of an embodiment of the present invention.

Computer 100 has a processor 102, which communicates with primary memory 104, input 106 and output 108. Computer 100 may optionally communicate with a network (not shown) or another device (not shown).

Processor 102 can be any suitable processor including microprocessors, as can be understood by persons skilled in the art. Processor 102 may include one or more processors for processing data and computer executable codes or instructions.

Memory 104 may include a primary memory readily accessible by processor 102 at runtime. The primary memory may typically include a random access memory (RAM) and may only need to store data at runtime. Memory 104 may also include a secondary memory, which may be a persistent storage memory for storing data permanently, typically in the form of electronic files. The secondary memory may also be used for other purposes known to persons skilled in the art. Memory 104 can include one or more computer readable media. For example, memory 104 may be an electronic storage comprising a computer readable medium for storing electronic data including computer executable codes. The computer readable medium can be any suitable medium accessible by a computer, as can be understood by a person skilled in the art. A computer readable medium may be either removable or non-removable, either volatile or non-volatile, including any magnetic storage, optical storage, or solid state storage devices, or any other medium which can embody the desired data including computer executable instructions and can be accessed, either locally or remotely, by a computer or computing device. Any combination of the above is also included in the scope of computer readable medium. Memory 104 may store computer executable instructions for operating computer 100 in the form of program code, as will be further described below. Memory 104 may also store data such as operational data, image data, input data, and output data.

Input 106 is to be broadly interpreted and may include user input devices for receiving user input such as image data and operation commands. Example user input devices may include a keyboard, a mouse, a disk drive/disk, a network communication device, a microphone, a scanner, a camera, and the like. Input 106 may also include sensors, detectors, or imaging devices for capturing, for example, an image. Input 106 may also include a communication device for communicating with a separate imaging device and receiving image data from the imaging device. Input 106 may communicate with another computer or device through wired or wireless communication, as can be understood by persons skilled in the art. An input device can be locally or remotely connected to processor 102, either physically or in terms of communication connection.

Similarly, output 108 is also to be broadly interpreted. Output 108 may include a display device such as a monitor for displaying output data, a printer for printing output data, a communication device for communicating output data to another computer or device, and the like, as can be understood by persons skilled in the art. Output 110 may also include other devices such as a computer writable medium and the device for writing to the medium. Like input device 106, an output device 108 can be local or remote.

It will be understood by those of ordinary skill in the art that computer 100 may also include other, either necessary or optional, components not shown in the FIG. 1.

The hardware in computer 100 may be manufactured and configured in any suitable manner, including that for a conventional computer with the exception that images are processed differently in computer 100 as will be described below. As can be understood, the imaging processing methods and algorithms may be implemented with either hardware, or a combination of hardware and software.

Memory 104 may store thereon computer executable code or instructions, which when executed by processor 102 can cause computer 100 to carry out any of the methods described herein or one or more steps of these method. The software for use in computer 100 may be readily developed and implemented by persons skilled in the art after reading this paper. As can be appreciated, methods described herein can also be carried out using a hardware device having circuits for performing one or more of the described calculations or functions.

Figure 2:
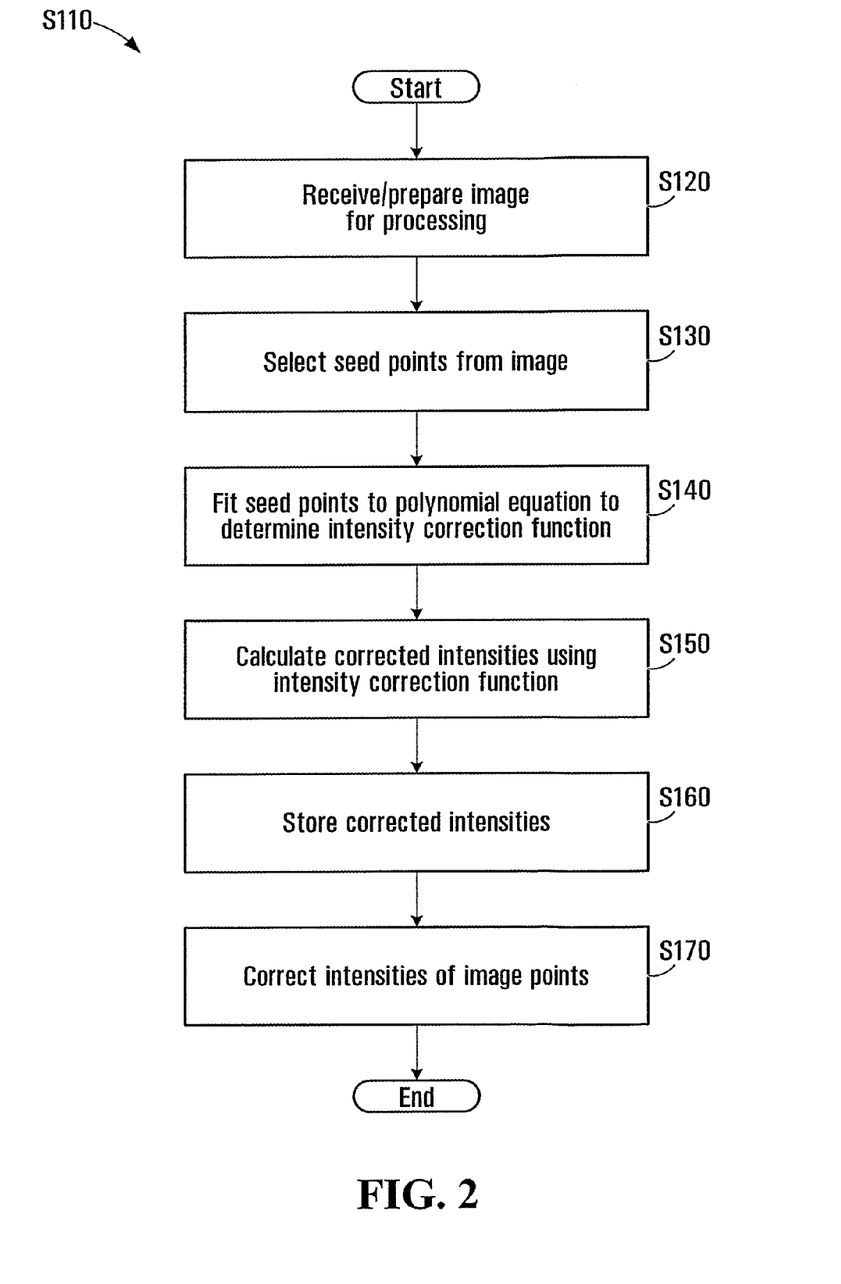
FIGS. 2 and 3 are flowcharts for a process of image correction.
Figure 3:
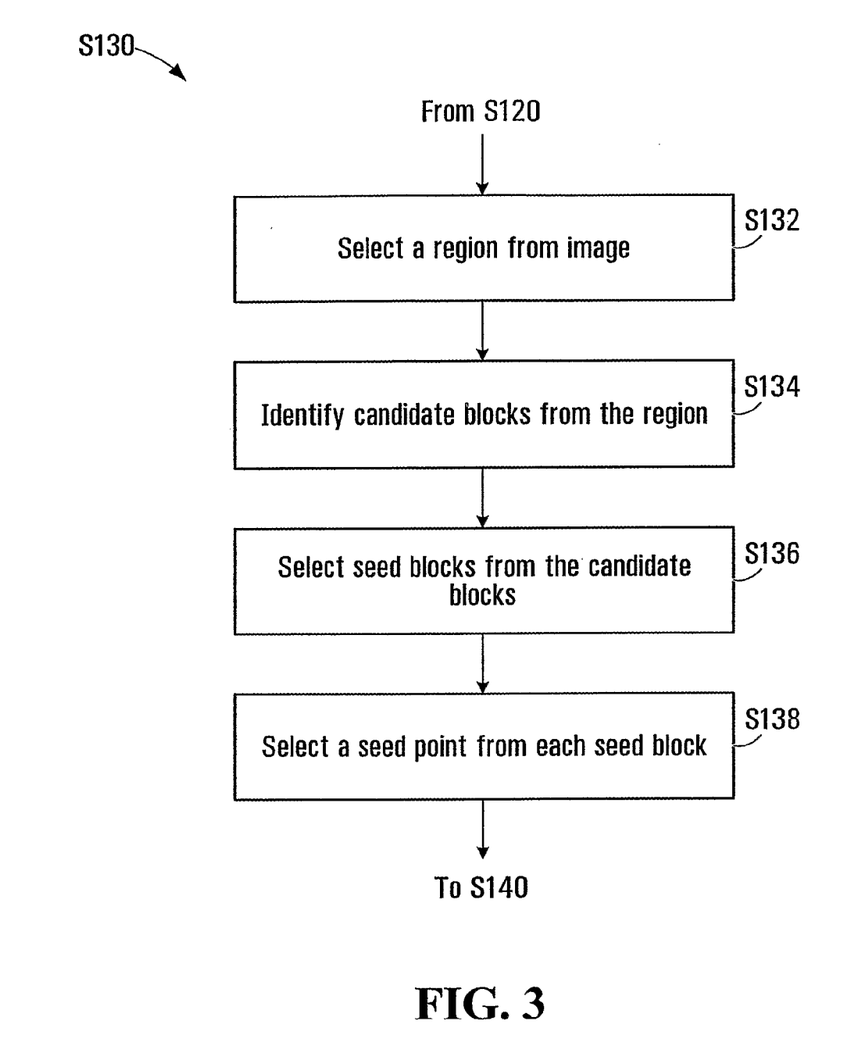

FIGS. 2 and 3 illustrate an exemplary image processing process S110 that can be carried out, at least in part, by or using computer 100. Process S110 is described below with reference also to FIGS. 4 to 15.

Figure 4:
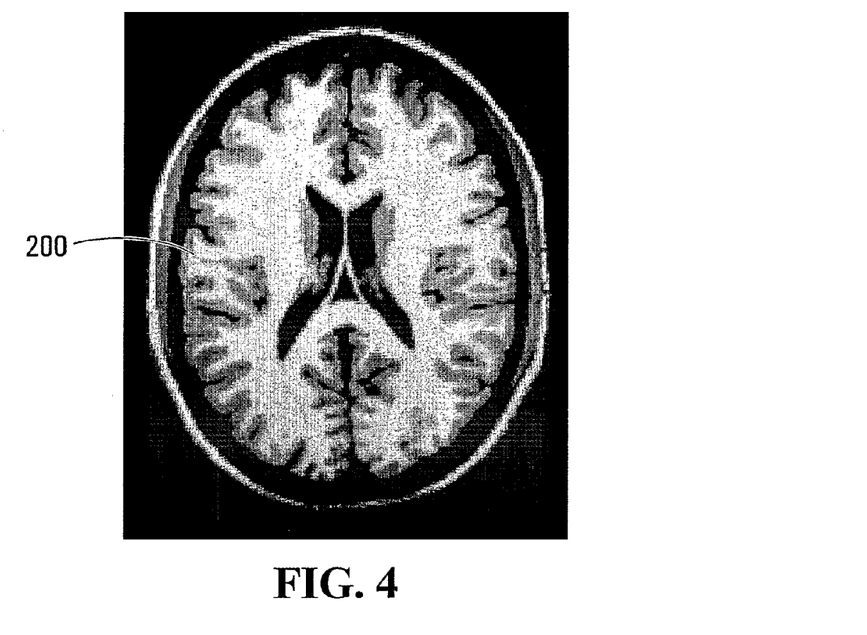
FIG. 4 is an MR brain image.

At S120, an MR image to be processed is received. For example, an image or image data for the image may be received in memory 104 of computer 100 through input 106. The image data may include coordinates of the image points and intensity values associated with the image points. The image points may be pixels in a 2D image or voxels in a 3D image. An exemplary 2D brain image 200 is shown in FIG. 4, which is a T1-weighted MR image. In image 200, brighter pixels are assumed to have higher image intensities. Typically, the brightest class of tissues in a T1-weighted MR image is the white matter. As can be seen and understood by persons skilled in the art, the field inhomogeneity effect is clearly visible in image 200, particularly in the bottom regions of the white matter regions where intensities of the image points gradually changes. Since the same class of tissue (here white matter) is expected to have the same intensity, the slow, smooth variation of intensity within the same class of tissue indicates field inhomogeneity. The class of tissue refers to the type of tissue that is represented by the image points. Typical tissue classes or types for brain images include grey matter, white matter, cerebrospinal fluid, meninx, bone, muscle, fat, skin, or air. In some patients, additional classes such as edema, tumor, hemorrhage or other abnormal classes may exist.

The image data may be presented in the form of an intensity histogram or the like. For example, the image may be expressed as $I_m(x)$, where x is the coordinate of each image point and $I_m(x)$ is the corresponding intensity at each point x. The coordinate symbol "x" is used herein to denote broadly any coordinate in any suitable coordinate system; and is not limited to the x-coordinate in the Cartesian coordinate system. For example, "x" may represent coordinates in all three dimensions of the Cartesian coordinate system for a 3D image or the coordinates in the two dimensions of a 2D image. x may also be an index number from which the actual coordinate can be derived.

Figure 5:
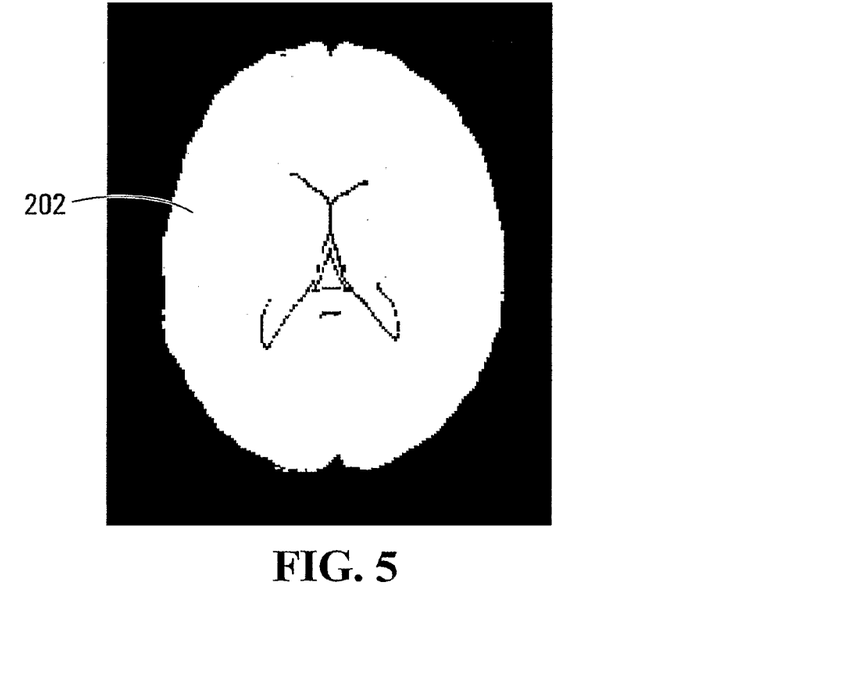
FIG. 5 is an image of a background mask for the MR brain image of FIG. 4.
Figure 6:
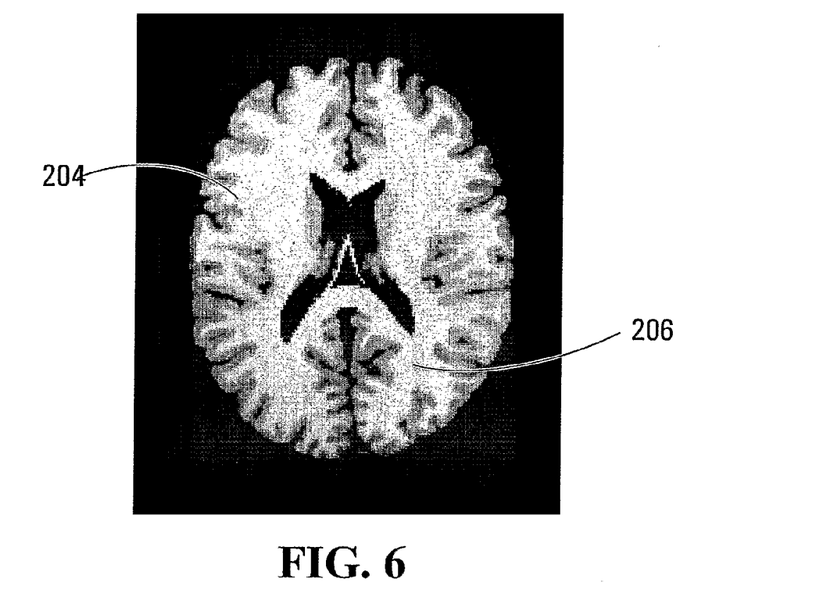
FIG. 6 is an image showing a region of interest segmented from the image of FIG. 4 using the mask of FIG. 5.

The received image may be optionally pre-processed. For example, certain background regions and a region of interest (ROI) may be identified. Background image points may be removed. As is typical in brain image analysis, the ROI may be first determined, either manually by a human or automatically by a machine such as a computer, or based on both human and computer input. As is conventional, the ROI may be identified by applying a background mask to the image such as image 200. An example mask 202 for image 200 is shown in FIG. 5. The mask may be obtained using any suitable technique including a conventional technique. Mask 202 is a binary image (black or white) generated according the technique described in Sandor and Leahy, "Surface-based labeling of cortical anatomy using a deformable atlas," *IEEE Transactions Medical Imaging*, 1990, vol. 17, no. 1, pp. 41-54, the contents of which are incorporated herein by reference. This technique has been implemented in a computer program, BrainSuite, by Dr. David W. Shattuckand. The software program is available from University of Southern California and downloadable online from <http://neuroimage.usc.edu/forums/>. The mask such as Mask 202 may be used to remove image points that do not need inhomogeneity correction or that will distort inhomogeneity correction. In the present example, mask 202 is used to remove scalp and skull image points and other image points that do not need inhomogeneity correction from image 200. The resulting image 204 of the brain after removal of scalp and skull is shown in FIG. 6.

At S130, seed points in the image are selected, as will be further described below. The number of seed points for an image may vary but should be sufficiently large so that a satisfactory statistical result may be obtained, as can be understood by persons skilled in the art. The seed points $x_s$ may be selected such that the true intensity ($I_t$) of all the seed points are expected to be the same, i.e., $I_t(x_s) \equiv I_s$, where $I_s$ is a coordinate-invariant constant. As can be appreciated, ideally, all tissues of the same class will have the same measured intensity and different classes of tissues will likely have different intensities, if the magnetic field is homogenous and there is no background noise. Thus, image points for a same tissue class are expected to have the same true intensity. As will become apparent below, selecting seed points from regions of the same tissue class can simplify the inhomogeneity correction process. The selection of seed points will be described in more detail below.

At S140, the measured intensity values of the seed points are fit to Equation (8). For the purpose of illustration, it is assumed below that the intensity correction function $I_{f2}(x)$ is used. Thus, Equation (8) can be expressed as, $$I_m(x_s) = [1 + f_2(x_s)]I_0 = [1 + f(x_s)]I_0. \tag{9}$$

The fitting determines the values of $I_0$ and p. It is noted the fitted value of $I_0$ is an approximation of the value of $I_s$, which is typically not a priori known. In a different embodiment, $I_{f2}(x)$ may be used, in which case Equation (8) becomes:

$$I_m(x_s) = I_0 + f_1(x_s) = I_0 + f(x_s). \tag{10}$$

The fitting may be carried out using a least-square fitting technique. Once the values of $I_0$ and p are determined, the intensity correction function $I_f(x)$ is determined. As can be appreciated, as the seed points are expected to have the same true intensity, the variation in intensity in the seed points may be assumed to be mainly due to field inhomogeneity, ignoring the effect of noise. The effect of noise is assumed to be ignorable, as the noise is random and with a sufficiently large sample of seed points the effect of noise on the final result is small due to statistical averaging. The effect of noise may be further reduced when the seed blocks are selected as described herein.

At S150, a corrected intensity $I_c(x)$ for each image point in the ROI is calculated according to Equation (2).

At S160, the calculated $I_c(x)$ are stored, such as in memory 104, for correcting the original image such as image 204. The values of $I_c(x)$ may be stored in memory 104. The stored intensities may be used to display a corrected image or for later use. For example, when stored for displaying, the corrected intensities may be stored in a RAM and be used to calculate the display data, which may be in turn stored in a display buffer for displaying the corrected image, such as on a computer monitor (not shown). The stored data may also be transferred to another computing device or location.

Figure 14:
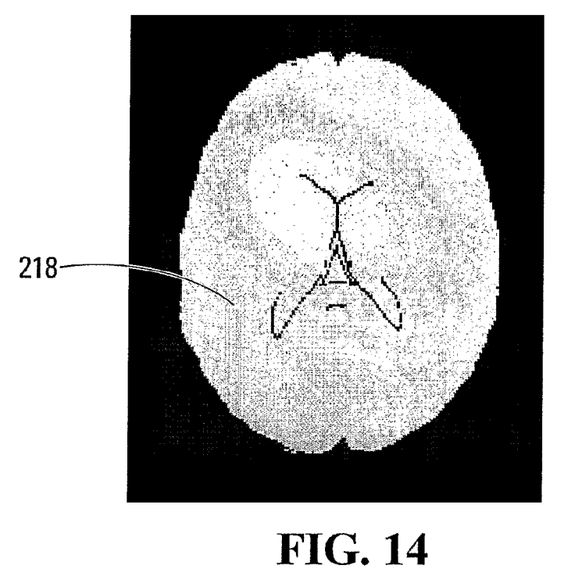
FIG. 14 is an inhomogeneity map extracted from the seed points selected from seed blocks of FIG. 12.

Alternatively, the calculated values of $I_f(X)$ or $f(x)$ may be stored and displayed. For example, when the form of $I_{f1}(x)$ is used in the fitting, the values of $I_{f1}(x)$ or $f_1(x)$ may be stored and directly plotted to expressly show the inhomogeneity intensity contributions. An exemplary plot of inhomogeneity intensities is shown in FIG. 14, which will be further described below.

At S170, the original image such as image 204 may be corrected by substituting $I_m(x)$ with $I_c(x)$ for the corresponding image points, when the intensity correction function $I_{f2}(x)$ is used in the fitting. Correcting the MR image may be performed by displaying, such as on a computer display, the corrected MR image using the corrected intensities, or by replacing the measured intensity values in an image data storage, such as an image file, with the corresponding corrected intensity values.

Figure 15:
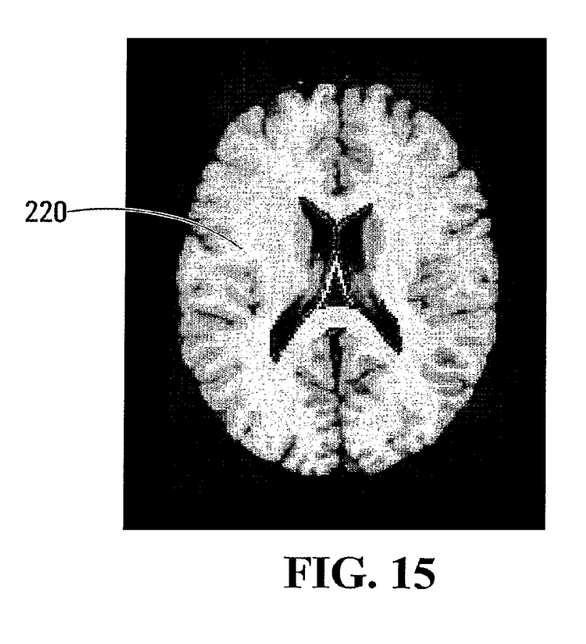
FIG. 15 is a corrected image corrected from the image of FIG. 3.

An exemplary corrected image 220 is shown in FIG. 15. The corrected image 220 can be obtained based on an exemplary process S130 of selecting seed points, as described next with reference to FIGS. 3 and 4 to 15.

At S132 of FIG. 3, a region for processing is selected from the MR image, which may or may not be pre-processed. For example, the ROI 202 in FIG. 6 determined earlier may be selected as the region to be processed. Alternatively, a region of a particular tissue type may be selected for processing. In the example shown in FIGS. 6 to 15, it is assumed that the ROI is the region to be processed. Seed points will be selected from the selected region to be processed. In many cases, it is difficult or inaccurate to determine whether a particular image point belongs to a particular tissue class based on only the intensity of the image point, due to the presence of noise and inhomogeneity, the effect of either of which is unknown at this point. To more accurately identify the image points that belong to the same tissue class, intensities of neighboring image points may also be considered, such as with the use of seed blocks and candidate seed blocks, as described below.

At S134, the ROI is divided into blocks and candidate seed blocks are identified from the region to be processed.

A block of image points refers to a set of image points that are adjacent to one another. The image points in a block may form any shape. For convenience of processing, the MR image may be divided into blocks that have the same shape and size. The size of a block may vary. In some embodiments, each image block may have equal image points in each dimension. For instance, an image block may have "S" image points in each dimension. Thus, if the image is 2D, each image block will be a square block having S×S number of image points. If the image is 3D, each image block will be a cube having S×S×S number of image points. In one embodiment, S may be 5. In another embodiment, S may be a different number such as from 3 to 9. The number of image points in each block may be determined by considering two balancing factors. On the one hand, a larger block is more likely to contain image points that belong to multiple tissue classes. On the other hand, random noise will affect the result more when each block has fewer image points. For MR brain images, it has been found that S=5 produces satisfactory results in some applications.

Figure 7:
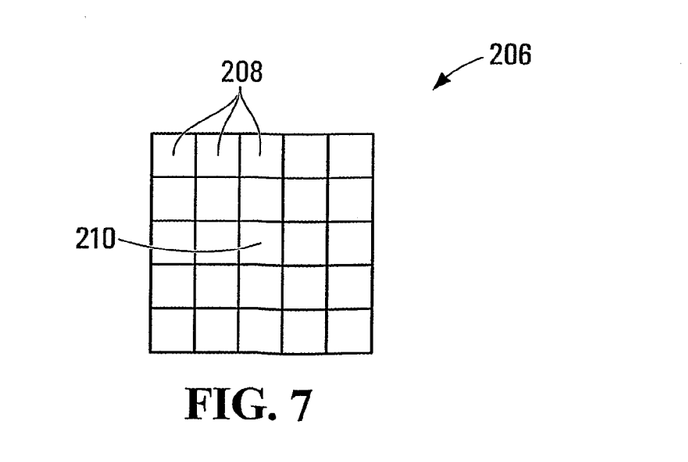
FIG. 7 is an enlarged view of a block of image points.

In the specific example illustrated in FIGS. 6 to 13, the MR image is divided into square blocks 206 all having the same size S=5. An exemplary block 206 is shown in image 204 of FIG. 6 and in FIG. 7. For simplicity, the intensity variation is not shown in FIG. 7. As can be seen, in this example, each block 206 is of a square shape. Each side of the square is formed of 5 image points 208. Each block 206 has a central image point 210. The block 206 shown in FIG. 7 is a 2D block but one of skill in the art can readily appreciate that 3D blocks can be similarly constructed for a 3D image, in which case, the blocks may have the shape of a cube, where each side of the cube is formed of a square such as the square shown in FIG. 7. The image points 208 are shown as square-shaped pixels but in different embodiments the image points may have other shapes, such as generally round or hexagon shaped in a 2D image. The shapes of the image points may be dictated by the imaging technique used to obtain the images. As can be understood, square and cube shaped image points and blocks may be convenient to process.

Candidate seed blocks are those blocks that have image points whose intensities fall within a given range so that they are likely to represent the same class of imaged matter, such as a tissue matter.

As can be appreciated, in a T1-weighted MR brain image, the brightest matter is typically the white matter. Thus, the image points in the brighter regions in FIG. 6, which are of relatively higher measured intensities, are expected to represent the white matter. As the white matter is the largest continuous component in the brain, it may be advantageous to select seed points that are expected to represent the white matter so that a good sample of the field points may be obtained better field. In a different embodiment, the seed points may be selected so that they are expected to represent a different class, such as grey matter or the like. Alternatively, the seed points may be selected so that they represent the particular class of imaged matter that is of primary interest for further analysis or processing.

Candidate blocks may be identified as follows.

As can be understood, a block may contain both background and tissue image points. Therefore, the blocks may be initially divided into background blocks and tissue blocks. A background block is a block that has a high percentage of background image points and a tissue block is a block that has a low percentage of background image points. For example, background image points may be those that have intensities less than a given background intensity threshold. Image points with intensities higher than the background threshold may be considered as tissue points. The background threshold may be determined according to any suitable technique. Many conventional techniques are well known and may be used for determining the background threshold. A percentage threshold may also be selected to divide the blocks into background blocks and tissue blocks. In one embodiment, the percentage threshold may be 30%, but another value may be used in a different embodiment. Thus, if the number of tissue points in a block is more than 70% of the total number of image points in the block, the block is classified as a tissue block. Otherwise, it is classified as a background block. Other techniques may also be used to divide the blocks into background and tissue blocks. While such division may not be necessary in some embodiments, it can improve the processing efficiency by eliminating blocks that will have no impact on the result at the outset.

In the following process, background blocks are ignored and only tissue blocks are subject to further processing.

Assuming there are "N" number of tissue blocks "w" in the selected region of the MR image. The blocks may be indexed using an index such as "i", such that a block "$w_i$" is the ith block, where i=1, ..., or N. It is also assumed that there are "M" number of distinct measured intensity values ($I_{m,I}$) for all the image points in the tissue blocks, which are ranked and indexed with the index "I", where I=1, ..., or M. For example, they may be ranked in ascending order so that $I_{m,1}$ is of the lowest value and $I_{m,M}$ is of the highest value. Under these assumptions, a given block $w_i$ has image points whose measured intensities have a number of values selected from the set of $I_{m,I}$. Assuming the minimum measured intensity in block $w_i$ is $I_{m,j}$ and the maximum is $I_{m,k}$, then $0 \leq j \leq k \leq M$ and $I_{m,j} \leq I_{m,k}$. The range of intensity in block $w_i$ is thus $R_i = I_{m,k} - I_{m,j}$.

As can be appreciated, if $R_i$ is large, the block $w_i$ is likely to have more than one types or classes of tissues. To select only blocks that contain one class, any blocks that have an intensity range ($R_i$) larger than a threshold value ($R_{th}$) may be removed from further consideration. Thus, the candidate blocks may be identified as those that satisfy the equation:

$$R_i < R_{th}. \tag{11}$$

As can be understood, in different embodiments another range statistic may be used to identify candidate blocks. For example, a normalized range statistic may be used. In one embodiment, candidate blocks may be identified as those that satisfy the equation:

$$R_i' < R'_{th}, \tag{12}$$

where $R_i'$ ($=I'_{m,k} - I'_{m,j}$) is a normalized intensity range for the ith block, and $I'_{m,k}$ and $I'_{m,j}$ are normalized intensities. In one embodiment, a normalized intensity may be normalized against the median intensity ($I_{m,M/2}$), such as by using a normalization factor $2I_{m,M/2}$. In another embodiment, the normalization factor may be the average intensity of all image points in the selected region. In the following, it is assumed that the intensities are normalized as:

$$I'_{m,I} = I_{m,I} / 2(I_{m,M/2}). \tag{13}$$

As can be understood, a normalized range statistic may be advantageous in some applications, as the normalized range statistic may be less sensitive to noise or systematic errors in intensity measurements.

The value of $R_{th}$ or $R'_{th}$ may be chosen so that a sufficient number of candidate blocks can be obtained and the candidate blocks have a sufficiently narrow intensity spread. When the threshold is too large, a candidate block may contain more than one tissue class. When the threshold is too small, few or no blocks can satisfy Equation (11) or (12). It has been found that with a normalized range statistic, such as normalized according to Equation (13), $R'_{th} = 0.5$ can produce satisfactory results in some embodiments.

Figure 8:
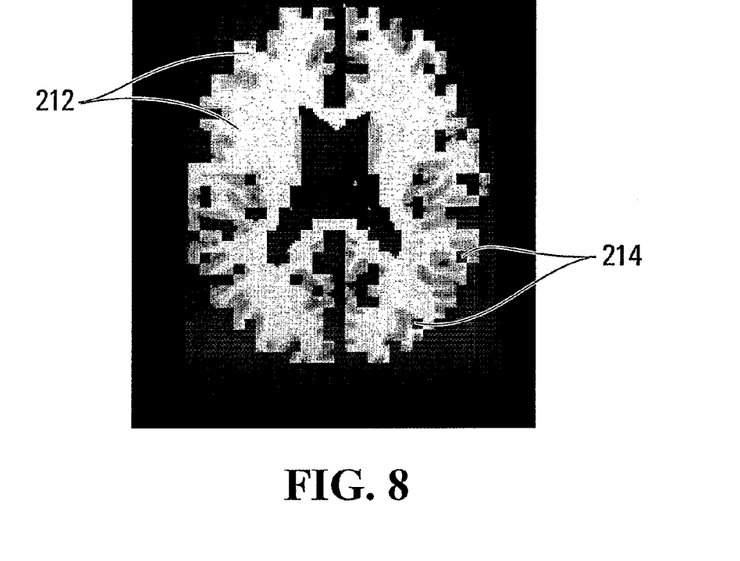
FIG. 8 is an image of initial candidate blocks identified from the image of FIG. 6 according to the method of FIGS. 2 and 3.

Therefore, in one embodiment, the chosen range statistic of each block in the ROI is calculated and normalized. Those blocks that have a normalized range statistic satisfying the Equation (12) are identified as the initial candidate blocks, where $R'_{th} = 0.5$. FIG. 8 shows candidate blocks 212 identified from image 204 of FIG. 6 according to this procedure. As shown, the candidate blocks 212 are not completely black and the non-candidate blocks 214 are shown in black.

As can be understood, each candidate block so identified contains one class of tissue but different candidate blocks do not necessarily contain the same class and may contain different classes. Further selections are thus made to select seed blocks which all contain the same class of tissue, at S136.

In one embodiment, the candidate blocks are first further filtered using a statistical metric. The statistical metric of a block may be a statistical average such as the mean, the median, or the trimmed mean of the intensities of the image points in the block. The statistical metric may also be the mode of the block, i.e. the most frequent intensity value for the image points in the block.

In a particular embodiment, the statistical metric may be the median. Assume a candidate block $w_i$ has a median $\mu_i$ and each its neighbor block (represented by $w_j$) has a median $\mu_j$. When the intended tissue class to be included in the seed blocks is the brightest class, a particular candidate block may be eliminated if Equation (14) is satisfied for at least one neighbor block, or equation (15) is satisfied for all neighbor blocks:

$$\mu_j - \mu_i > \Delta, \tag{14}$$

$$\mu_i - \mu_j > \Delta, \tag{15}$$

where $\Delta > 0$ is a threshold value. In one embodiment, $\Delta$ may be 30. Another value of $\Delta$ may be used in a different embodiment. The value of $\Delta$ may be selected and tested, and then adjusted based on the test results. When Equation (14) is satisfied for at least one neighbor block, the candidate block $w_i$ likely has a class of tissue that is not the brightest since at least one neighbor block has a brighter median. When Equation (15) is satisfied, the candidate block $w_i$ is an isolated block as all neighbor blocks are darker. As can be appreciated, after the above process of elimination, the remaining candidate blocks form a continuous region and the absolute difference between the average intensities of each pair of neighbouring candidate blocks is less than the threshold, $\Delta$.

As can be appreciated, for different types of MR images, the brightest and darkest classes of tissues may be different. To select seed blocks for a class of tissue that has a different intensity ranking, Equations (14) and (15) may need to be modified. For example, for selecting seed blocks for a darker class of tissue, the order of $\mu_j$ and $\mu_i$ may be switched, as can be understood by person skilled in the art.

A further elimination of blocks may be made by conducting an inter-block statistical analysis. An intensity metric of each candidate block is calculated and a distribution histogram of the metric for all remaining candidate blocks is obtained. The histogram is analyzed to determine a range in the histogram which contains the largest peak in the histogram and is dominant in the histogram. Any block having a value of the metric that is outside the determined range is eliminated as a background block. As can be appreciated, in T1-weighted images, the cerebrospinal fluid is darker than grey and white matter and thus contributes little to brighter regions. In one embodiment, the range may be selected to include 80% of the blocks. Thus, 20% of the blocks that have the lowest metric values are removed. In this case it is expected that the removed blocks contain mainly cerebrospinal fluid or grey matter.

Figure 9:
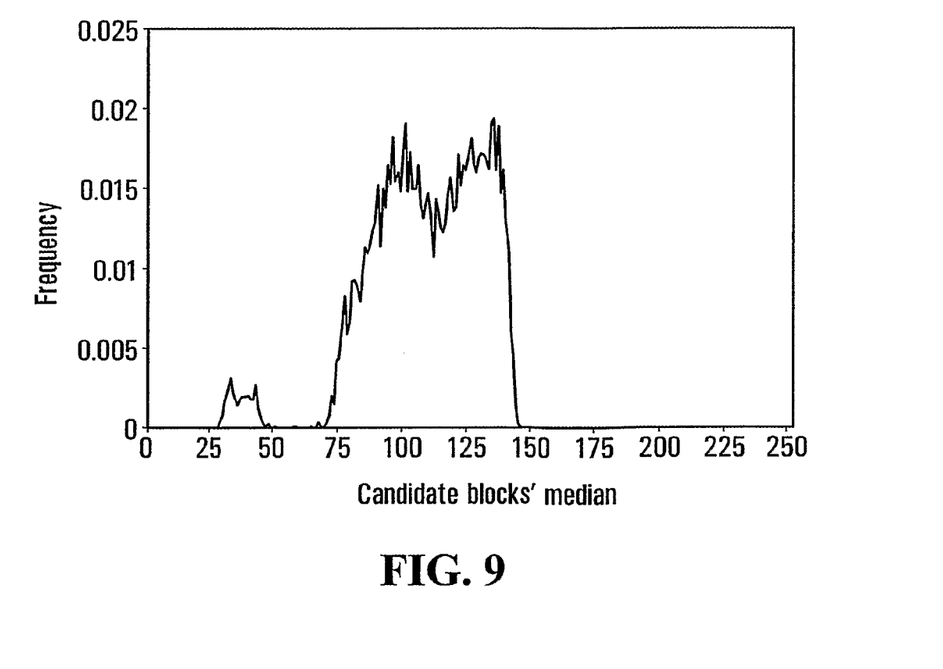
FIG. 9 is a histogram of a statistical metric for the candidate blocks of FIG. 8.
Figure 10:
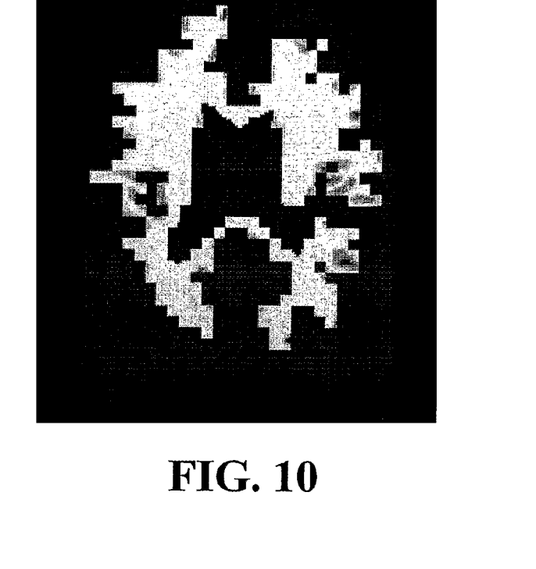
FIG. 10 is an image of remaining candidate seed blocks selected from the initial candidate blocks shown in FIG. 8.
Figure 11:
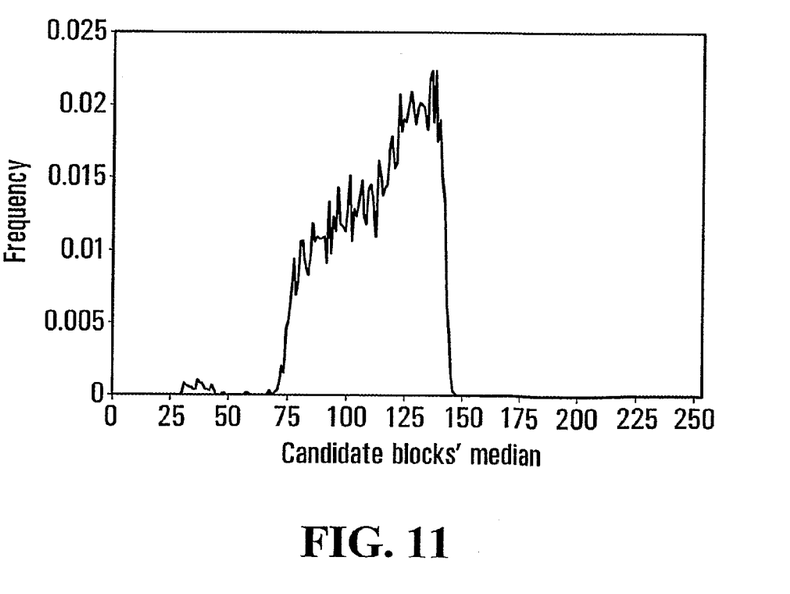
FIG. 11 is a histogram of the statistical metric for the candidate blocks of FIG. 10.

FIG. 9 is a histogram of an intensity metric for the initial candidate blocks shown in FIG. 8, where the metric is the median intensity of each candidate block. The x-axis is the intensity metric and the y-axis is the frequency of blocks that have a certain value of the intensity metric. FIG. 10 shows the candidate blocks that remain after removal of blocks based on the statistical analysis described above. FIG. 11 is a histogram for the remaining candidate blocks of FIG. 10. As can be seen, the continuous region formed by the candidate blocks are dominated by one class of imaged matter, the white matter.

The candidate blocks may be further filtered based on the assumption that the same class of tissue should be connected. Thus, any new isolated candidate blocks, which may become isolated as a result of the elimination of certain initial candidate blocks described above, are identified and removed. For example, any candidate block that is not connected to another candidate block may be identified and eliminated. In one embodiment, two blocks are connected if they are 8-connected in a 2D image or 26-connected in a 3D image. Connected blocks are also called neighbor blocks.

If at this point, there is still a large number of candidate blocks, the candidate blocks may be simply downsized to reduce computation time. For instance, at this point, one of any two neighboring candidate blocks may be removed. Or, if two candidate blocks are close to each other, one of them may be removed. Removing closely located blocks will not adversely affect the final result because the field inhomogeneity is assumed slow varying over space. The number of final seed blocks may be selected depending on the particular application and available computing resource.

Figure 12:
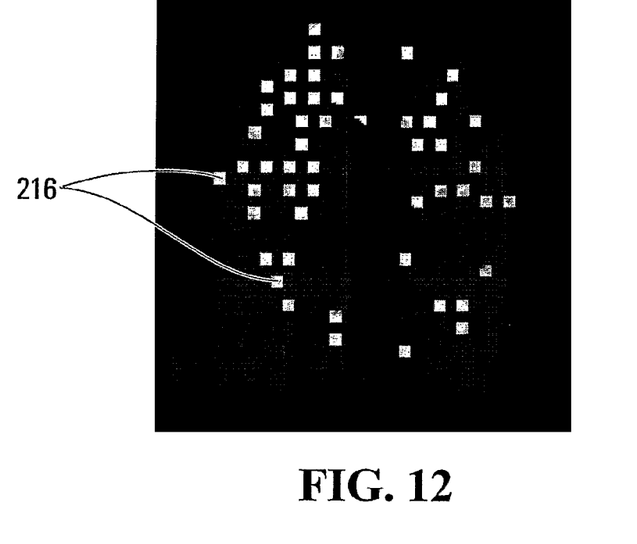
FIG. 12 is an image of seed blocks selected from the candidate blocks of FIG. 10.
Figure 13:
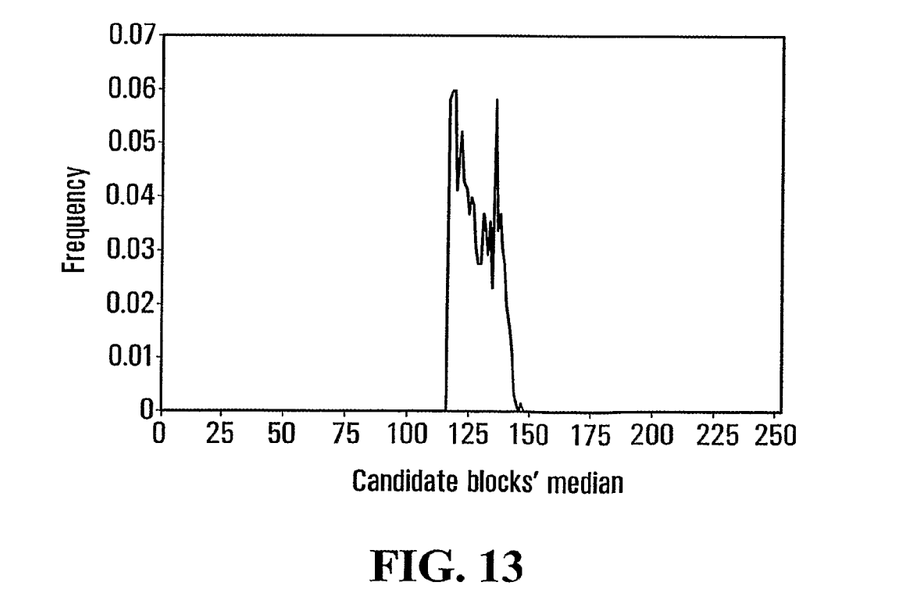
FIG. 13 is a histogram of the statistical metric for the seed blocks of FIG. 12.

FIG. 12 shows the seed blocks 216 remaining after such further removal and downsizing from the image of FIG. 10. As can be seen, the seed blocks are distributed throughout the region formed by candidate blocks in FIG. 10 (the expected white matter region) and are isolated from each other. In this example, the number of candidate blocks is reduced from 3832 in FIG. 10 to 653 in FIG. 12. For comparison, the histogram for FIG. 12 is shown in FIG. 13. As shown, the distribution of the intensity metric among the seed blocks are quite uniform and are within a narrow range.

At S138 of FIG. 3, the seed image points are selected from the seed blocks 216. In one embodiment, only the central point in each seed block is selected as the seed point. In other embodiments, any other point in the seed block may be selected, or more than one point may be selected. As can be understood, the particular position of the seed point in each seed block should have no material effect on the final result.

Once the seed points are selected, the fitting at S140 may be performed to determine the intensity correction function $l_f(x)$, by fitting the measured intensities of the seed points to Equation (8). An exemplary inhomogeneity intensity map 218 is plotted in FIG. 14, where the intensities shown in the ROI are values of $l_f(x)$. The regions outside the ROI are shown as black. The map 218 indicates that the magnetic field is slowly varying and the field inhomogeneity is more pronounced at the bottom region of the map 218.

When the intensity correction function $l_f(x)$ is determined, a corrected image may be obtained, where the corrected image includes corrected image points, which have corrected intensity values calculated from Equation (2). The corrected image may be displayed or stored, such as in memory 104. The corrected image may be stored in a display memory such as a display buffer for a monitor. The corrected image or other values calculated based on $l_f(x)$ may be stored in memory 104 either temporarily or permanently for correcting the MR image. The stored data may simply include values of the coefficients of the intensity correction function for later use. The stored data may also, or alternatively, include data calculated from the intensity correction function. For example, the values of corrected intensities calculated according to Equation (2) may be stored. As discussed before, it may not be necessary to calculate or store corrected intensities for all image points in the MR image in some embodiments.

The calculated or stored values may be used to display a corrected MR image. For example, the corrected image 220 in FIG. 15 is obtained by substituting the original measured intensities in image 200 of FIG. 6 with the calculated corrected intensities for the corresponding image points. As can be seen, the corrected image 220 gives a more accurate representation of the true image intensities of the brain tissues than the original image 200 does. As field inhomogeneity is effectively removed, the intensity in a particular region representing a particular tissue class, such as the white matter, is quite uniform.

The above procedure may be implemented and performed automatically using a computer program containing computer executable instructions. The program may be written in any suitable computer language as can be understood by person skilled in the art. The program may be stored in memory 104 such that when the computer executable instructions are loaded at process 102, computer 100 is caused to perform the above procedure. The result of the process, such as the fitted coefficients and the corrected image intensities, may be stored in memory 104 or may be transmitted to another computer through output 108. The result may also be displayed on a computer monitor or any other display for a user to view, as illustrated in FIGS. 14 and 15.

As can be appreciated, the process and method described above may have certain advantages over a conventional inhomogeneity correction technique. In particular, it is not necessary to remove noise, as discussed above. The effect of noise is reduced when the seed points are not selected individually but from seed blocks that are statistically representative of a class of imaged matter. The correction process according to an embodiment of the present invention may also be performed relatively quickly, such as 10 to 60 times faster than conventional inhomogeneity correction techniques.

The embodiments of the present invention may be applicable in many fields and is not limited to brain image analysis. For example, any MR images where field inhomogeneity is present may be corrected according an embodiment of the present invention. The process discussed above may be readily modified by persons skilled in the art for a different type of MR image depending on the particular application.

For clarify, the word "or" is used in this description in the conjunctive or explanatory sense, but not in the disjunctive sense unless otherwise specified.

Of course, the above described embodiments are intended to be illustrative only and in no way limiting. The described embodiments are susceptible to many modifications of form, arrangement of parts, details and order of operation. The invention, rather, is intended to encompass all such modification within its scope, as defined by the claims.

What is claimed is:

1. In a computer including a memory, and a processor for executing computer implemented code stored in said memory, a computer implemented method of correcting a magnetic resonance (MR) image comprising a plurality of image points, each having a coordinate x and a measured intensity $l_m(x)$ dependent on x, said method comprising:

selecting seed points having a same expected true intensity from said image points, each seed point having a coordinate $x_s$;

determining an intensity correction function $l_f(x)$ by fitting measured intensities of said seed points $l_m(x_s)$, to $l_m(x_s) = l_f(x_s)$, wherein $l_f(x)$ is a non-zero order polynomial function having coefficients, wherein values of said coefficients are determined by said fitting; and obtaining a corrected image comprising corrected image points, each corrected image point having a coordinate $x_c$ and a corrected intensity $l_c(x_c)$, $l_c(x_c)$ being calculated according to $l_c(x_c) = l_m(x_c)/l_f(x_c)$, wherein $l_f(x_c)$ is the determined polynomial function $l_f(x)$ applied to coordinate $x_c$ and $l_m(x_c)$ is an initial value of a measured intensity at said coordinate $x_c$.

2. The method of claim 1, comprising storing values of said coefficients of said intensity correction function.

3. The method of claim 1, comprising storing values of $l_f(x)$.

4. The method of claim 1, comprising storing said corrected image.

5. The method of claim 1, comprising displaying said corrected image.

6. The method of claim 1, comprising correcting said MR image by substituting the measured intensity $l_m(x_c)$ with the corrected intensity $l_c(x_c)$ for said corrected image points.

7. The method of claim 1, wherein $l_f(x)$ is a second order polynominal.

8. The method of claim 1, wherein $l_f(x)$ has a form selected from $l_{f1}(x)=l_0+f(x)$ and $l_{f2}(x)=[1+f(x)]l_0$, where $f(x)$ is a non-zero order polynomial function, and $I_0$ is one of said coefficients determined by said fitting.

9. The method of claim 8, wherein (i) said coordinate x comprises Cartesian x, y and z coordinates, and $$f(x)=f(x,y,z)=p_{1,0,0}x+p_{0,1,0}y+p_{0,0,1}z+p_{2,0,0}x^2+p_{0,2,0}y^2+p_{0,0,1}z^2+p_{1,1,0}xy+p_{1,0,1}xz+p_{0,1,1}yz; \text{ or}$$

(ii) said coordinate x comprises Cartesian x and y coordinates, and $$f(x)=f(x,y)=p_{1,0}x+p_{0,1}y+p_{2,0}x^2+p_{0,2}y^2+p_{1,1}xy.$$

10. The method of claim 1, wherein said plurality of image points represent a plurality of classes of imaged tissue, said selecting seed points comprising:

selecting seed blocks from a continuous region in said MR image, said continuous region dominated by image points representing one class of imaged tissue, each seed block having a plurality of image points; and selecting an image point from said each seed block as one of said seed points.

11. The method of claim 10, wherein exactly one of said seed points is selected from each one of said seed blocks.

12. The method of claim 10, wherein each one of said seed blocks has a central image point, and said selecting an image point comprises selecting said central image point as one of said seed points.

13. The method of claim 10, wherein said seed blocks are isolated from each other.

14. The method of claim 10, wherein said seed blocks are distributed throughout said continuous region.

15. The method of claim 10, wherein said seed blocks have a same shape and a same size.

16. The method of claim 15, wherein said MR image is three-dimensional and said shape is a cube.

17. The method of claim 16, wherein said cube consists of 125 image points.

18. The method of claim 15, wherein said MR image is two-dimensional and said shape is a square.

19. The method of claim 18, wherein said square consists of 25 image points.

20. The method of claim 10, wherein said continuous region is formed of candidate blocks, and said step of selecting seed blocks comprises:

identifying said candidate blocks from said MR image, said identifying comprising determining blocks that each includes image points having measured intensities of a range statistic less than a range threshold; and selecting said seed blocks from said candidate blocks.

21. The method of claim 20, wherein said range threshold is selected so that image points in each candidate block are expected to represent one class of imaged tissue.

22. The method of claim 20, wherein said range statistic is a normalized range statistic.

23. The method of claim 22, wherein said normalized range statistic is less than 0.5.

24. The method of claim 20, wherein each candidate block neighbors at least another candidate block.

25. The method of claim 20, wherein image points in each candidate block have an average intensity, and an absolute difference between the average intensities of each pair of neighboring candidate blocks is less than a threshold.

26. The method of claim 1, wherein said plurality of image points of said MR image are within a region of interest in said MR image.

\* \* \* \* \*